(12) United States Patent
Delaney, Jr. et al.

(10) Patent No.: US 12,178,888 B2
(45) Date of Patent: *Dec. 31, 2024

(54) REACTIVE MULTI-ARM POLYMERS HAVING BRANCHED END GROUPS

(71) Applicant: Boston Scientific Scimed Inc., Maple Grove, MN (US)

(72) Inventors: Joseph T. Delaney, Jr., Minneapolis, MN (US); Kolbein K. Kolste, Boxboro, MA (US); Tatyana Dyndikova, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 504 days.

This patent is subject to a terminal disclaimer.

(21) Appl. No.: 16/999,871

(22) Filed: Aug. 21, 2020

(65) Prior Publication Data

US 2021/0060183 A1 Mar. 4, 2021

Related U.S. Application Data

(60) Provisional application No. 62/892,798, filed on Aug. 28, 2019.

(51) Int. Cl.
| | | |
|---|---|---|
| A61K 49/04 | (2006.01) | |
| A61L 27/52 | (2006.01) | |
| A61L 27/58 | (2006.01) | |
| C08J 3/24 | (2006.01) | |
| C08L 39/06 | (2006.01) | |
| C08L 71/02 | (2006.01) | |
| C08L 101/00 | (2006.01) | |

(52) U.S. Cl.
CPC .............. *A61K 49/04* (2013.01); *A61L 27/52* (2013.01); *A61L 27/58* (2013.01); *C08J 3/24* (2013.01); *C08L 101/005* (2013.01); *C08L 39/06* (2013.01); *C08L 71/02* (2013.01); *C08L 2201/06* (2013.01)

(58) Field of Classification Search
CPC .... A61K 49/04; A61K 31/43; A61K 49/0442; A61K 49/0457; A61K 51/06; A61K 51/1213; A61L 27/52; A61L 27/58; C08J 3/24; C08L 101/005; C08L 39/06; C08L 71/02; C08L 2201/06; C08L 79/02; C08G 73/028
See application file for complete search history.

(56) References Cited

U.S. PATENT DOCUMENTS

| | | | | |
|---|---|---|---|---|
| 6,566,406 | B1 * | 5/2003 | Pathak | A61K 47/34 424/78.17 |
| 6,818,018 | B1 | 11/2004 | Sawhney | |
| 8,383,161 | B2 | 2/2013 | Campbell et al. | |
| 11,326,022 | B2 * | 5/2022 | Delaney, Jr. | C08F 8/14 |
| 2011/0142936 | A1 | 6/2011 | Campbell et al. | |

FOREIGN PATENT DOCUMENTS

| | | | | |
|---|---|---|---|---|
| CA | 2716091 A1 * | 4/2011 | ......... | A61L 24/0031 |
| EP | 2196193 A1 * | 6/2010 | ....... | A61B 17/00491 |
| WO | 2011123591 A1 | 10/2011 | | |

OTHER PUBLICATIONS

Fu et al. Bioconjugate Chem. 2006, 17, 1043-1056. (Year: 2006).*
Chao, M., et al. "The use of TraceIT® as a fiducial marker in bladder radiotherapy." Int J Urol 23 (2016): 47. (Year: 2016).*
Lapienis, Star-shaped polymers having PEO arms, Progress in Polymer Science, vol. 34, Issue 9, 2009, pp. 852-892. (Year: 2009).*
Longmire, Michelle, Peter L. Choyke, and Hisataka Kobayashi. "Dendrimer-based contrast agents for molecular imaging." Current topics in medicinal chemistry 8.14 (2008): 1180-1186. (Year: 2008).*
Fu, Y.; Nitecki, D. E.; Maltby, D.; Simon, G. H.; Berejnoi, K.; Raatschen, H. J.; Yeh, B. M.; Shames, D. M.; Brasch, R. C., Dendritic iodinated contrast agents with PEG-cores for CT imaging: synthesis and preliminary characterization. Bioconjug. Chem. 2006, 17 (4), 1043-56.
Krause, W.; Hackmann-Schlichter, N.; Maier, F. K.; Muller, R., Dendrimers in diagnostics. Top. Curr. Chem.2000, 210 (Dendrimers II), 261-308.
International Search Report and Written Opinion for the International Patent Application No. PCT/US2020/047450, mailed Nov. 25, 2020, 11 pages.
"Augmenix Announces Positive Three-year SpaceOAR Clinical Trial Results," Imaging Technology News, Oct. 27, 2016.
"Augmenix Receives FDA Clearance to Market its TraceIT™ Tissue Marker," BusinessWire Jan. 28, 2013.

* cited by examiner

*Primary Examiner* — Mina Haghighatian
*Assistant Examiner* — Janice Y Silverman
(74) *Attorney, Agent, or Firm* — Seager, Tufte & Wickhem LLP (57) ABSTRACT

In some aspects, the present disclosure pertains to a polymer that comprises a plurality of polymer arms, wherein a first portion of the polymer arms comprise a reactive end group and wherein a second portion of the polymer arms comprise a branched end group that comprise a plurality of covalently attached diagnostic and/or therapeutic groups, which may be, for example, radiocontrast groups or radioactive groups. Other aspects pertain to a system that comprises (a) a first composition comprising such a polymer and (b) a second composition comprising a multifunctional compound that comprises reactive functional groups that are reactive with the reactive end group of the multi-arm polymer. Still other aspects pertain to a crosslinked reaction product of (a) such a polymer and (b) a multifunctional compound that comprises functional groups that are reactive with the reactive end group of the multi-arm polymer.

13 Claims, 7 Drawing Sheets

REACTIVE MULTI-ARM POLYMERS HAVING BRANCHED END GROUPS

CROSS-REFERENCE TO RELATED APPLICATION

This application claims the benefit of U.S. Provisional Application No. 62/892,798, entitled "REACTIVE MULTI-ARM POLYMERS HAVING BRANCHED END GROUPS" and filed Aug. 28, 2019, the entire disclosure of which is incorporated herein by reference.

FIELD

The present disclosure relates to reactive multi-arm polymers having branched end groups, to compositions containing such polymers, to methods of making such polymers, and to methods of using such polymers, among other aspects. The reactive multi-arm polymers of the present disclosure are useful, for example, in various biomedical applications.

BACKGROUND

Bioerodible injectable hydrogels are a newly emerging class of materials having a variety of medical uses.

As one specific example, in the case of SpaceOAR®, a long-term bioerodible injectable hydrogel based on multi-arm PEG-based, such products are used to create or maintain space between tissues in order to reduce side effects of off-target radiation therapy. See "Augmenix Announces Positive Three-year SpaceOAR Clinical Trial Results," *Imaging Technology News*, Oct. 27, 2016. As another specific example, Augmenix has developed TraceIT® Hydrogel, a bioerodible injectable hydrogel synthetic hydrogel consisting primarily of water and iodinated cross-linked polyethylene glycol (PEG) that is visible under CT, cone beam, ultrasound and MR imaging and is useful as a tissue marker (e.g., for targeted radiation therapy). See "Augmenix Receives FDA Clearance to Market its TraceIT™ Tissue Marker," *Business Wire* Jan. 28, 2013. TraceIT® hydrogel remains stable and visible in tissue for three months, long enough for radiotherapy, after which it is absorbed and cleared from the body. Id.

There is a continuing need in the biomedical arts for further hydrogels, including therapeutic and/or diagnostic hydrogels, for precursors of such hydrogels, for methods of making such hydrogels and precursors, for methods of using such hydrogels and precursors, and for systems for forming such hydrogels, among other needs.

SUMMARY

In some aspects of the present disclosure, a multi-arm polymer comprising a plurality of polymer arms is provided, wherein a first portion of the polymer arms comprise a reactive end group and wherein a second portion of the polymer arms comprise a branched end group comprising a plurality of covalently attached diagnostic and/or therapeutic groups.

In some embodiments, the covalently attached diagnostic and/or therapeutic groups are radiocontrast groups or are radioactive groups.

In some embodiments, which can be used in conjunction with the above aspects and embodiments, the radiocontrast groups comprise a monocyclic or multicyclic aromatic structure that comprises a plurality of radiopaque functional groups (e.g., iodine groups) and a plurality of hydrophilic functional groups.

In some embodiments, which can be used in conjunction with the above aspects and embodiments, radioactive groups comprise a monocyclic or multicyclic aromatic structure that comprises a plurality of radionuclide groups (e.g., carbon-11, nitrogen-13, fluorine-18, iodine-131 gallium-67, indium-111, or thallium-201 groups, among others) and a plurality of hydrophilic functional groups.

In some embodiments, which can be used in conjunction with the above aspects and embodiments, the radiopaque functional groups or the radionuclide groups are iodine groups.

In some embodiments, which can be used in conjunction with the above aspects and embodiments, the plurality of hydrophilic functional groups are selected from one or more of $C_1$-$C_4$-hydroxyalkyl groups, $C_1$-$C_4$-aminoalkyl groups or $C_1$-$C_4$-carboxyalkyl groups.

In some embodiments, which can be used in conjunction with the above aspects and embodiments, the branched end group comprises 3 or more branches.

In some embodiments, which can be used in conjunction with the above aspects and embodiments, the branched end group is a dendritic end group.

In some embodiments, which can be used in conjunction with the above aspects and embodiments, the branched end group comprises an acyclic or cyclic hydroxy-polycarboxylic residue core, an acyclic or cyclic polyamine residue core, an oligolysine residue core, or a polyamidoamine core.

In some embodiments, which can be used in conjunction with the above aspects and embodiments, the polymer arms are composed of one or more types of hydrophilic monomers.

In some embodiments, which can be used in conjunction with the above aspects and embodiments, the polymer arms are composed of one or more types of monomers selected from N-vinyl pyrrolidone, hydroxyethyl acrylate, hydroxyethyl methacrylate, PEG methyl ether acrylate, PEG methyl ether methacrylate and ethylene oxide.

In some embodiments, which can be used in conjunction with the above aspects and embodiments, the plurality of polymer arms extends from a polyol residue core.

In some embodiments, which can be used in conjunction with the above aspects and embodiments, the reactive end group is selected from one of an electrophilic group and a nucleophilic group.

In other aspects of the present disclosure, a composition is provided that comprises a multi-arm polymer in accordance with any of the above aspects and embodiments.

In some embodiments, the first portion of the polymer arms corresponds to between 60% and 99% of a total number of the polymer arms in the composition (e.g., ranging anywhere from 60% to 70% to 80% to 90% to 95% to 98% to 99% of the total number of polymer arms) and the second portion of the polymer arms corresponds to between 1% and 40% of the total number of polymer arms in the composition (e.g., ranging anywhere from 1% to 2% to 5% to 10% to 20% to 30% to 40% of the total number of polymer arms).

In some embodiments, which can be used in conjunction with the above aspects and embodiments, the composition further comprises a therapeutic agent and/or a contrast agent.

In other aspects of the present disclosure, a system is provided that comprises (a) a first composition comprising a multi-arm polymer in accordance with any of the above aspects and embodiments and (b) a second composition comprising a multifunctional compound that comprises functional groups that are reactive with the reactive end group of the multi-arm polymer.

In some embodiments, the first portion of the polymer arms may correspond to between 60% and 99% of the total number of polymer arms in the first composition (e.g., ranging anywhere from 60% to 70% to 80% to 90% to 95% to 98% to 99% of the total number of polymer arms) and the second portion of the polymer arms may correspond to between 1% and 40% of the total number of polymer arms in the first composition (e.g., ranging anywhere from 1% to 2% to 5% to 10% to 20% to 30% to 40% of the total number of polymer arms).

In some embodiments, which can be used in conjunction with the above aspects and embodiments, the reactive end group is selected from one of electrophilic groups and nucleophilic groups and the functional groups are selected from the other of the electrophilic groups and nucleophilic groups.

In some embodiments, which can be used in conjunction with the above aspects and embodiments, the reactive end group is an electrophilic group and the functional groups are nucleophilic groups.

In some embodiments, which can be used in conjunction with the above aspects and embodiments, the nucleophilic groups are amine groups.

In some embodiments, which can be used in conjunction with the above aspects and embodiments, the second composition comprises a polyamine.

In some embodiments, which can be used in conjunction with the above aspects and embodiments, the polyamine comprises three or more amine groups.

In some embodiments, which can be used in conjunction with the above aspects and embodiments, the system further comprises a delivery device. In certain of these embodiments, the delivery device comprises a first reservoir containing the first composition and a second reservoir containing the second composition.

In some embodiments, which can be used in conjunction with the above aspects and embodiments, the first composition further comprises a therapeutic agent and/or a contrast agent.

In other aspects of the present disclosure, a crosslinked reaction product of (a) a multi-arm polymer in accordance with any of the above aspects and embodiments and (b) a multifunctional compound that comprises functional groups that are reactive with the reactive end group of the multi-arm polymer is provided.

DETAILED DESCRIPTION

The present disclosure relates to reactive multi-arm polymers having branched end groups (e.g., having two, three, four, five, six, seven, eight, nine, ten or more branches).

In various aspects, the present disclosure pertains to reactive multi-arm polymers that comprise a plurality of polymer arms (e.g., having two, three, four, five, six, seven, eight, nine, ten or more arms), wherein polymer arms of the multi-arm polymers comprise (a) a reactive end group, (b) a branched end group having a plurality of covalently attached diagnostic and/or therapeutic groups, or (c) both (a) and (b).

In various embodiments, the present disclosure pertains to reactive multi-arm polymers that comprise a plurality of polymer arms, wherein a first portion of the polymer arms comprise a reactive end group and wherein a second portion of the polymer arms comprise a branched end group having a plurality of covalently attached diagnostic and/or therapeutic groups.

In some embodiments, compositions containing the reactive multi-arm polymers may be provided in which the first portion of the polymer arms comprising the reactive end group may correspond to between 60% and 99% of the total number of polymer arms in the composition (e.g., ranging anywhere from 60% to 70% to 80% to 90% to 95% to 98% to 99% of the total number of polymer arms) and the second portion of the polymer arms comprising the branched end group may correspond to between 1% and 40% of the total number of polymer arms in the composition (e.g., ranging anywhere from 1% to 2% to 5% to 10% to 20% to 30% to 40% of the total number of polymer arms).

In various embodiments, the covalently attached diagnostic and/or therapeutic groups are radiocontrast agents that comprise a radiopaque moiety, for instance, a radiopaque moiety such as a halide (e.g., iodine, etc.) moiety, which renders the polymers visible under x-ray imaging, or a radioactive moiety (e.g., carbon-11, nitrogen-13, fluorine-18, iodine-131 gallium-67, indium-111, or thallium-201 groups, among others), which renders the polymers suitable, for example, for radiation therapy or for radio-diagnostic applications (e.g., positron emission tomography).

In certain embodiments, the covalently attached diagnostic and/or therapeutic groups are radiopaque aromatic moieties that comprise a monocyclic or multicyclic aromatic structure that comprises a plurality of radiopaque functional groups and, optionally, a plurality of hydrophilic functional groups. For example, the monocyclic or multicyclic aromatic structure may be selected from a benzene group and a naphthalene group, among others. The radiopaque functional groups may comprise, for example, iodide groups. Moreover, the plurality of hydrophilic functional groups may be selected from one or more of $C_1$-$C_4$-hydroxyalkyl groups, $C_1$-$C_4$-aminoalkyl groups or $C_1$-$C_4$-carboxyalkyl groups, among others.

In certain embodiments, the covalently attached diagnostic and/or therapeutic groups are radioactive aromatic moieties that comprise a monocyclic or multicyclic aromatic structure that comprises a plurality of radioisotopes and, optionally, a plurality of hydrophilic functional groups. For example, the monocyclic or multicyclic aromatic structure may be selected from a benzene group and a naphthalene group, among others. The radioisotopes may be selected from carbon-11, nitrogen-13, fluorine-18, iodine-131, gallium-67, indium-111, or thallium-201, among others. Moreover, the plurality of hydrophilic functional groups may be selected from one or more of $C_1$-$C_4$-hydroxyalkyl groups, $C_1$-$C_4$-aminoalkyl groups or $C_1$-$C_4$-carboxyalkyl groups, among others.

In various embodiments, the polymer arms are hydrophilic polymer arms. Such hydrophilic polymer arms may be composed of any of a variety of synthetic, natural, or hybrid synthetic-natural polymers including, for example, poly(alkylene oxides) such as poly(ethylene oxide) (also referred to as PEG), poly(propylene oxide) or poly(ethylene oxide-co-propylene oxide), poly(vinylpyrrolidone), polyoxazolines including poly(2-alkyl-2-oxazolines) such as poly(2-methyl-2-oxazoline), poly(2-ethyl-2-oxazoline) and poly(2-propyl-2-oxazoline), poly(vinyl alcohol), poly(allyl alcohol), poly(ethyleneimine), poly(allylamine), poly(vinyl amine), poly(amino acids), polysaccharides, and combinations thereof.

In some embodiments, the polymer arms extend from a core region. In certain of these embodiments, the core region comprises a residue of a polyol that is used to form the polymer arms. Illustrative polyols may be selected, for example, from straight-chained, branched and cyclic aliphatic polyols including straight-chained, branched and cyclic polyhydroxyalkanes, straight-chained, branched and cyclic polyhydroxy ethers, including polyhydroxy polyethers, straight-chained, branched and cyclic polyhydroxyalkyl ethers, including polyhydroxyalkyl polyethers, straight-chained, branched and cyclic sugars and sugar alcohols, such as glycerol, mannitol, sorbitol, inositol, xylitol, quebrachitol, threitol, arabitol, erythritol, adonitol, dulcitol, fucose, ribose, arabinose, xylose, lyxose, rhamnose, galactose, glucose, fructose, sorbose, mannose, pyranose, altrose, talose, tagatose, pyranosides, sucrose, lactose, and maltose, oligomers (defined herein as ranging from two to ten units, including dimers, trimers, tetramers, pentamers, hexamers, heptamers, octamers, enneamers and decamers) of straight-chained, branched and cyclic sugars and sugar alcohols and polymers (defined herein as eleven or more units) of straight-chained, branched and cyclic sugars and sugar alcohols, including the preceding sugars and sugar alcohols, starches, amylose, dextrins, cyclodextrins, as well as polyhydroxy crown ethers, and polyhydroxyalkyl crown ethers. Illustrative polyols also include aromatic polyols including 1,1,1-tris(4'-hydroxyphenyl) alkanes, such as 1,1,1-tris(4-hydroxyphenyl)ethane, and 2,6-bis(hydroxyalkyl)cresols, among others.

In certain beneficial embodiments, the polyol is an oligomer of a sugar alcohol such as glycerol, mannitol, sorbitol, inositol, xylitol, or erythritol, among others.

In certain beneficial embodiments, the polyol may contain two, three, four, five, six, seven, eight, nine, ten or more hydroxyl groups.

In certain embodiments, the first portion of the polymer arms comprise reactive end groups selected from an electrophilic group and a nucleophilic group.

In certain embodiments, the reactive end groups may be nucleophilic groups selected from amine groups and/or thiol groups.

In certain embodiments, the reactive end groups may be electrophilic groups selected from imidazole esters, imidazole carboxylates, benzotriazole esters, or imide esters, including N-hydroxysuccinimidyl esters. A particularly beneficial reactive end group is an N-hydroxysuccinimidyl ester group, which is used in various embodiments below.

Such polymer may be made via several strategies. In some strategies, a branched compound that comprises a plurality of diagnostic and/or therapeutic groups is covalently attached to a pre-existing multi-arm polymer.

Figure 1:
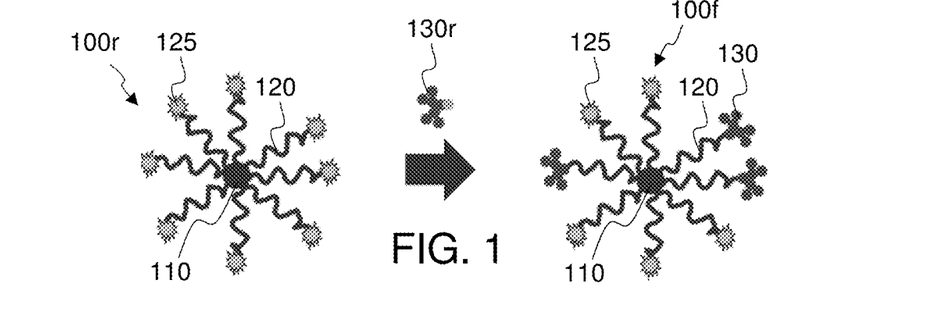
FIG. 1 is a schematic illustration of a method of forming reactive multi-arm polymers having branched end groups, in accordance with an embodiment of the present disclosure.

For example, in one strategy illustrated schematically in FIG. 1, a multi-arm polymer 100$m$ comprising a core region 110 (e.g., a polyol residue, among other possibilities) and a plurality of polymer arms 120 (e.g., a plurality of polyethylene oxide arms, among other possibilities) each having a reactive end group 125 (e.g., an amine-reactive group such as an N-hydroxysuccinimidyl ester group, among others) may be reacted with a sub-stoichiometric amount of a coupleable branched compound 130$r$ that comprises a plurality of covalently attached diagnostic and/or therapeutic groups and a functional group (e.g., an amine group) that is reactive with the reactive end group 125 of the multi-arm polymer 100$m$. The result is the formation of a multi-arm polymer 100$f$ that contains a plurality of the reactive end groups 125 that were initially present on the multi-arm polymer 100$m$ as well as a plurality of covalently attached branched end groups 130, each covalently attached branched end group 130 comprising a plurality of covalently attached diagnostic and/or therapeutic groups.

In particular embodiments, the reactive multi-arm polymer 100$r$ in the prior paragraph may be formed by reacting hydroxyl end groups of a multi-arm precursor polymer with a cyclic anhydride (e.g., glutaric anhydride, succinic anhydride, malonic anhydride, etc.) to form a reaction product in the form of a multi-arm polymer in which the polymer arms are terminated in a moiety that comprises a carboxylic acid group and a hydrolysable ester group positioned between the carboxylic acid group and the polymer arm. Subsequently, this reaction product may be treated with a coupling agent (e.g., a carbodiimide coupling agent such as N,N'-dicyclohexylcarbodiimide (DCC), 1-Ethyl-3-(3-dimethylaminopropyl)carbodiimide (EDC), N-Hydroxybenzotriazole (HOBt), BOP reagent, and/or another coupling agent) and N-hydroxysuccinimide, to yield a reactive multi-arm polymer 100$r$ comprising succinimidyl end groups 125, in particular, a reactive multi-arm polymer that comprises plurality of polymer arms that comprise a moiety that comprises a hydrolysable ester group and a reactive succinimide ester group.

Figure 2:
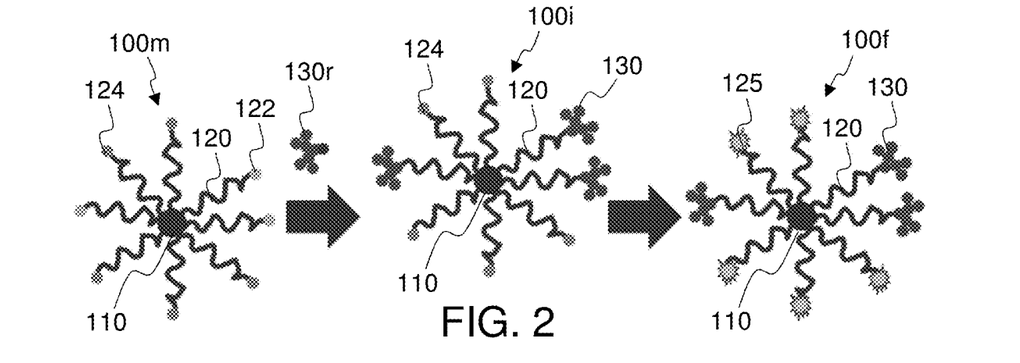
FIG. 2 is a schematic illustration of another method of forming reactive multi-arm polymers having branched end groups, in accordance with another embodiment of the present disclosure.

In another strategy, illustrated schematically in FIG. 2, a multi-arm polymer 100$m$ is shown which comprises a core region 110 (e.g., a polyol residue, among other possibilities) and a plurality of polymer arms 120 (e.g., a plurality of polyethylene oxide arms, among other possibilities), a fraction of the polymer arms having a first reactive end group 122 (e.g., an amino end group, among many other possibilities) and a remaining fraction of the polymer arms having a second functional group 124 (e.g., a hydroxyl group, among many other possibilities). This multi-arm polymer 100$m$ may be reacted with a coupleable branched compound 130$r$ that comprises a plurality of covalently attached diagnostic and/or therapeutic groups and a functional group (e.g., an amine-reactive group such as an N-hydroxysuccinimidyl ester group, among others) that is reactive with the first reactive end group 122 of the multi-arm polymer 100m. The result is the formation of an intermediate multi-arm polymer 100i that contains a plurality of second functional groups 124 (e.g., hydroxyl groups) that were present on the multi-arm polymer 100m, as well as a plurality of covalently attached branched moieties 130, each comprising a plurality of covalently attached diagnostic and/or therapeutic groups.

Subsequently, a reactive multi-arm polymer 100f having reactive end groups 125 (e.g., an amine-reactive group such as a succinimidyl ester group, among others) can be formed by converting the second functional groups 124 (e.g., hydroxyl groups) of the intermediate multi-arm polymer 100i into reactive end groups 125 (e.g., succinimidyl ester groups).

For example, in particular embodiments, the reactive multi-arm polymer 100f may be formed by reacting the hydroxyl end groups of the intermediate multi-arm polymer 100i with a cyclic anhydride (e.g., glutaric anhydride, succinic anhydride, malonic anhydride, etc.) to form a reaction product in the form of a multi-arm polymer in which a portion of the polymer arms are terminated in a moiety that comprises a carboxylic acid group and a hydrolysable ester group positioned between the carboxylic acid group and the polymer arm. Subsequently, this reaction product may be treated with a coupling agent (e.g., a carbodiimide coupling agent selected from those described above) and N-hydroxysuccinimde, to yield a multi-arm polymer comprising succinimidyl end groups 125, in particular, a multi-arm polymer that comprises plurality of polymer arms, a first portion of which comprise a moiety that comprises a hydrolysable ester group and a reactive succinimide ester group 125 and a second portion of which comprise a covalently attached branched moiety 130 that comprises a plurality of covalently attached diagnostic and/or therapeutic groups. In this embodiment, to the extent that the covalently attached branched moieties 130 may contain hydroxyl groups, such groups may be protected at some point prior to exposure to the N-hydroxysuccinimde and subsequently deprotected. (For example, where the covalently attached branched moiety 130 comprises hydroxyl groups on adjacent carbon atoms, these hydroxyl groups may be protected by reaction with 2,2-dimethoxypropane to form an acetonide-protected compound and subsequently deprotected by exposing the protected compound to slightly acidic pH conditions.)

Various strategies will now be described for forming coupleable branched moieties for use in the present disclosure.

Figure 4A:
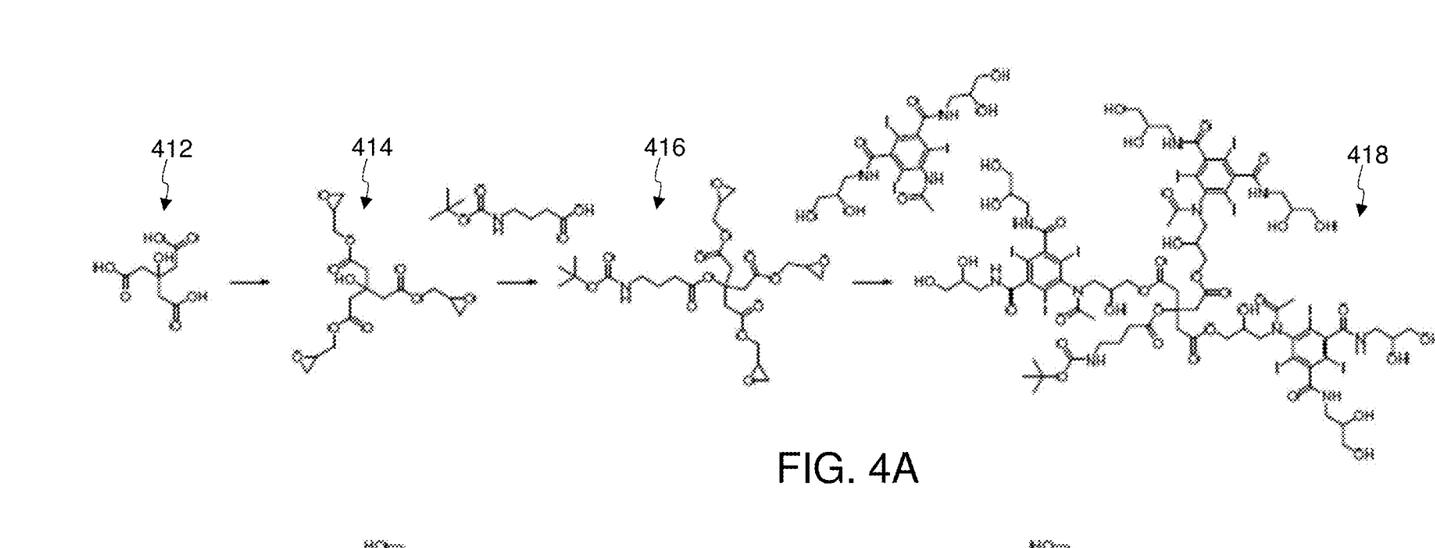
FIGS. 4A-4B schematically illustrate a method of forming a branched radiopaque amine-functionalized compound, in accordance with an embodiment of the present disclosure.
Figure 4B:
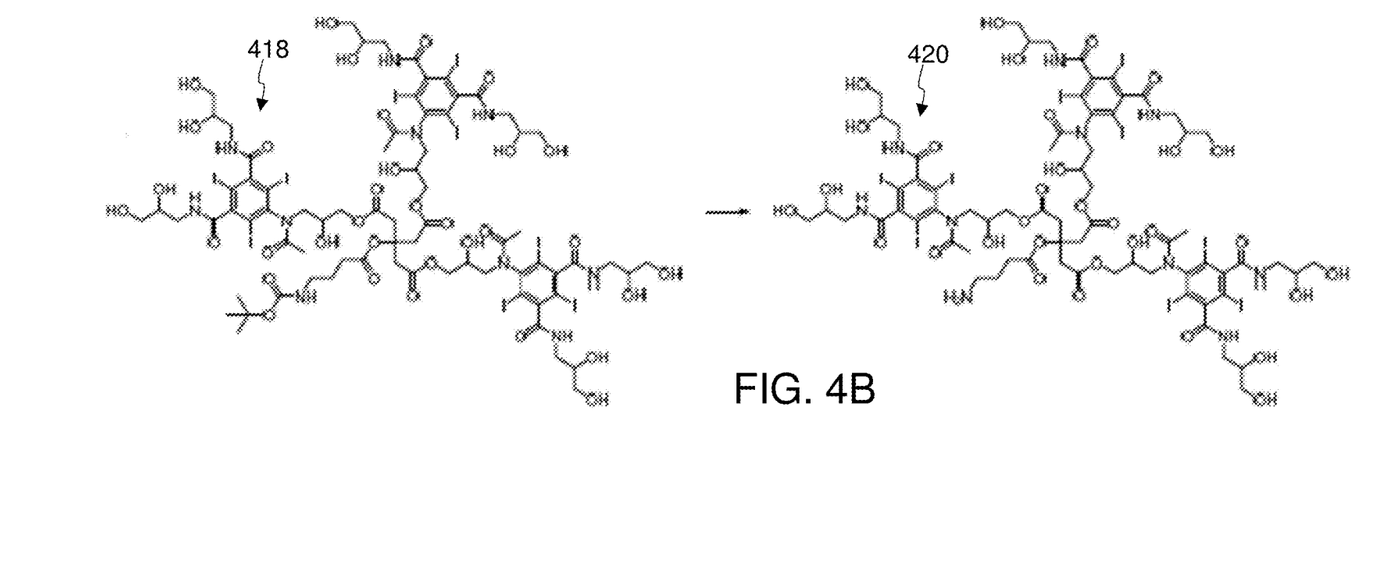

For example, in a convergent synthesis approach shown in FIG. 4A, a hydroxy-polycarboxylic acid, 412 (citric acid is shown, but others including malic acid or tartaric acid, may likewise be employed) is reacted with epichlorohydrin to form a first intermediate compound 414 having a plurality of triglycidyl ester groups, while retaining the hydroxide group that from the hydroxy-poly-carboxylic acid. The first intermediate compound 414 is then reacted with a suitable compound to form a second intermediate compound 416 having a tert-butyloxycarbonyl (tBoc) group at the position previously occupied by of the hydroxyl group. (For example, the first intermediate compound 414 may be reacted with a tBoc-protected aminobutyric acid as shown.) This first intermediate compound 414 is then reacted with a suitable iodinated compound, for example, a hydrophilic acetomido-substituted iodinated compound such as CAS no. 3117-80-7, also known as Iohexol Related Compound A, which is shown, or 5-acetamido-$N^1$,$N^3$-bis(2,3-dihydroxypropyl)-2,4,6-triiodo-$N^1$-methylisophthalamide (CAS no. 76350-28-2, also known as Iopromide Related Compound B) to form a further intermediate 418 having a tBoc group. Then, as shown in FIG. 4B, the further intermediate compound 418 can be treated with trifluoroacetic acid (TFAA) and/or gentle heating, thereby forming a primary amine group.

The resulting compound 420, which has three branches arising and a hydroxyacid reside core, can then be used as a coupleable branched compound 130r that comprises a plurality of covalently attached diagnostic and/or therapeutic groups (e.g., iodinated groups) and a functional group (e.g., a primary amine) that is reactive with a reactive end group 125 (e.g., a succinimidyl ester group) of a multi-arm polymer 100m, along the lines shown in FIG. 1. For example, by employing a sub-stoichiometric amount of the compound 420 relative to the reactive end groups 125, a multi-arm polymer 100f can be formed, which contains a plurality of the reactive end groups 125 that were initially present on the multi-arm polymer 100m as well as a plurality of covalently attached branched end groups 130.

Figure 5A:
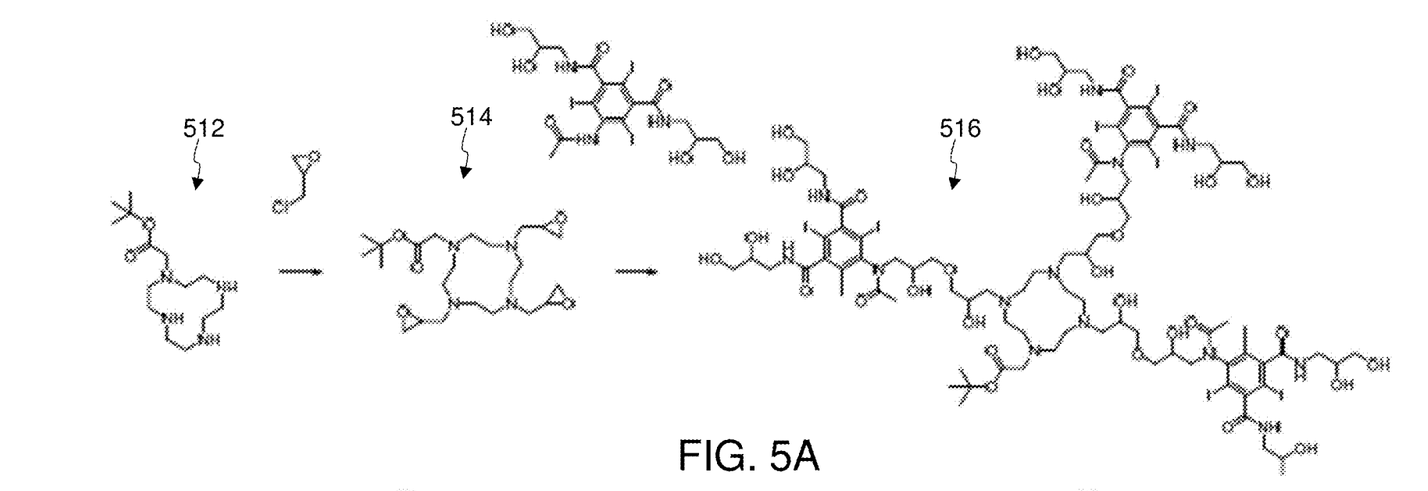
FIGS. 5A-5B schematically illustrate a method of forming a branched radiopaque amine-functionalized compound, in accordance with another embodiment of the present disclosure.
Figure 5B:
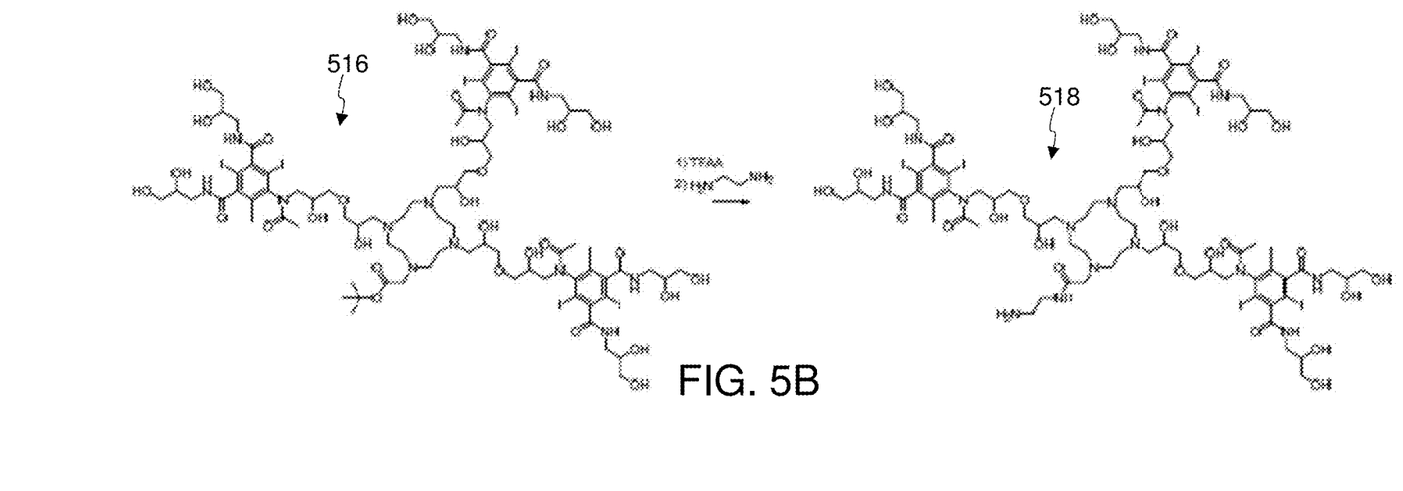

In another embodiment shown in FIGS. 5A-5B, a tBoc protected cyclic polyamine 512 (e.g., 1,4,7,10-tetraazacyclododecane-1-acetic acid, 1,1-dimethylethyl ester, CAS No. 137145-75-6) is reacted with epichlorohydrin to form a tBoc-protected polyepoxide intermediate compound 514, which is then reacted with a suitable iodinated species, for example, a hydrophilic acetomido-substituted iodinated species such as CAS no. 3117-80-7 (Iohexol Related Compound A) or 5-acetamido-$N^1$,$N^3$-bis(2,3-dihydroxypropyl)-2,4,6-triiodo-$N^1$-methylisophthalamide (CAS no. 76350-28-2) to form a further intermediate compound 516, Then, as shown in FIG. 5B, the intermediate compound 516 is treated with trifluoroacetic acid (TFAA), followed by reaction with a diamine (e.g., ethylenediamine), which cleaves the tert-butyloxy group and forms an amino ethyl amide group.

As with compound 420, the resulting compound 518, which has three branches and a cyclic polyamine residue core, can then be used as a coupleable branched compound 130r that comprises a plurality of covalently attached diagnostic and/or therapeutic groups (i.e., iodinated groups) and a functional group (i.e., a primary amine) that is reactive with the reactive end group 125 (i.e., a succinimidyl ester group) of a multi-arm polymer 100m, along the lines shown in FIG. 1. For example, by employing a sub-stochiometric amount of the compound 518 relative to the reactive end groups 125, a multi-arm polymer 100f can be formed, which contains a plurality of the reactive end groups 125 that were initially present on the multi-arm polymer 100m as well as a plurality of covalently attached branched end groups 130.

Figure 6A:
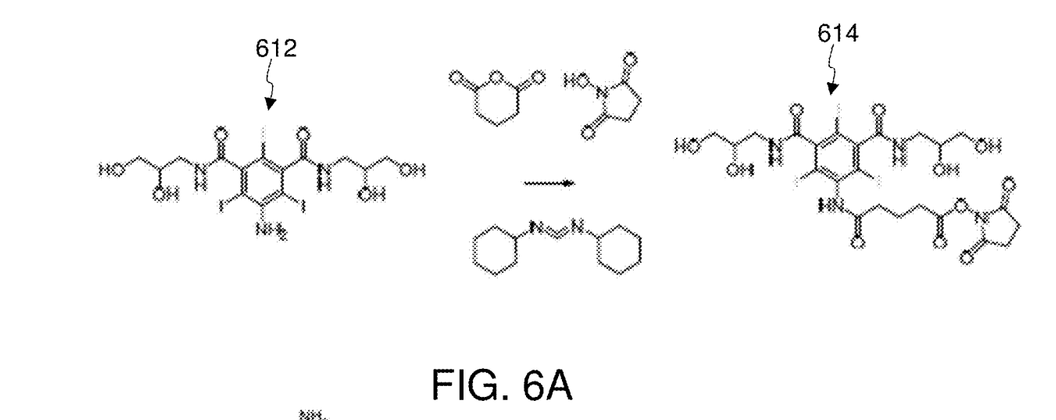
FIGS. 6A-6B is schematically illustrate method of forming a radiopaque oligo-lysine-based branched compound, in accordance with an embodiment of the present disclosure.
Figure 6B:
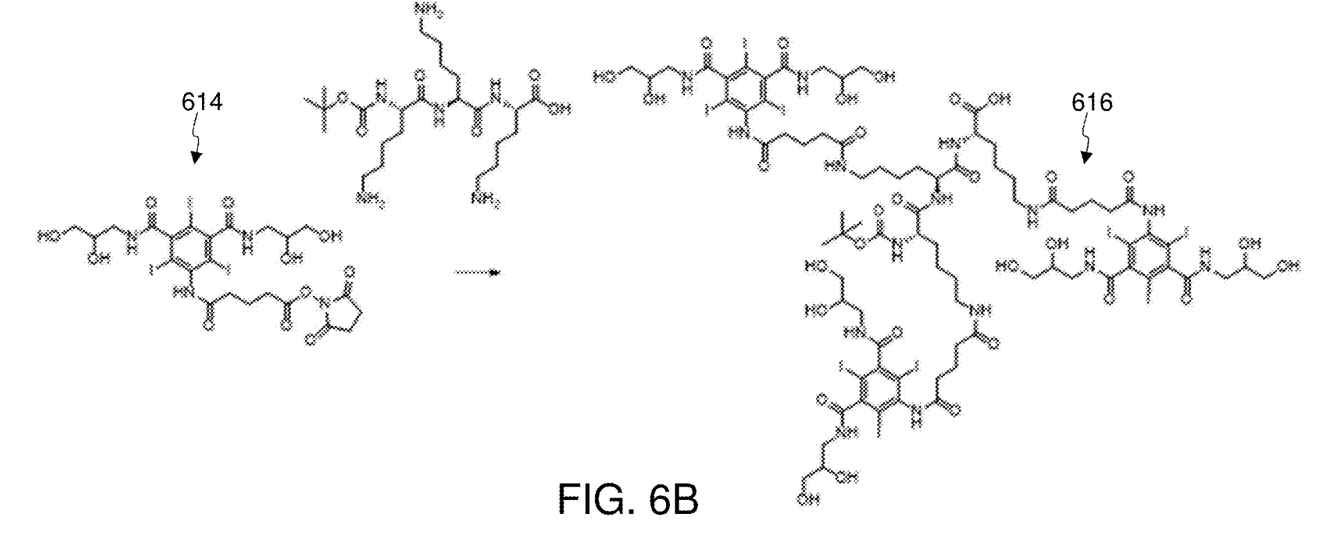

In another approach shown in FIGS. 6A-6B, an amino-substituted iodinated compound (e.g., a hydrophilic amino-substituted triiodoaniline compound 612, such as 5-amino-$N^1$,$N^3$-bis(2,3-dihydroxypropyl)-2,4,6-triiodoisophthalamide (CAS No. 76801-93-9) or 5-amino-$N^1$,$N^3$-bis(2,3-dihydroxypropyl)-2,4,6-triiodo-$N^1N^3$-dimethylisophthalamide (CAS No. 69232-66-2)) is functionalized with succinimidyl glutarate groups. More particularly, the triiodoaniline compound 612 may be reacted with a cyclic anhydride (e.g., succinic anhydride), followed by reaction with N-hydroxysuccinimde in the presence of a suitable coupling agent (e.g., N,N'-dicyclohexylcarbodiimide), thereby forming a succinimidyl-glutarate-substituted triiodoaniline compound 614. Then, as shown in FIG. 6B, the succinimidyl-glutarate-substituted triiodoaniline compound 614 is reacted with a polyamine compound, in particular an oligolysine molecule (tBoc-protected trilysine is shown) to form the compound 616, which has three branches and an oligolysine residue core. Note that the additional lysine repeat units will lead to additional branching (e.g., a tetralysine oligomer will lead to four branches, a pentalysine oligomer will lead to five branches, a hexalysine oligomer will lead to six branches, etc.). Subsequently, the compound 616 may be treated along the lines described in conjunction with FIG. 5B to cleave the tert-butyloxy group and forms a primary amine group. Such a compound can then be used as a coupleable branched compound 130r that comprises a plurality of covalently attached diagnostic and/or therapeutic groups (i.e., iodinated groups) and a functional group (i.e., a primary amine) that is reactive with the reactive end group 125 (i.e., a succinimidyl ester group) of a multi-arm polymer 100m, along the lines shown in FIG. 1.

Figure 7A:
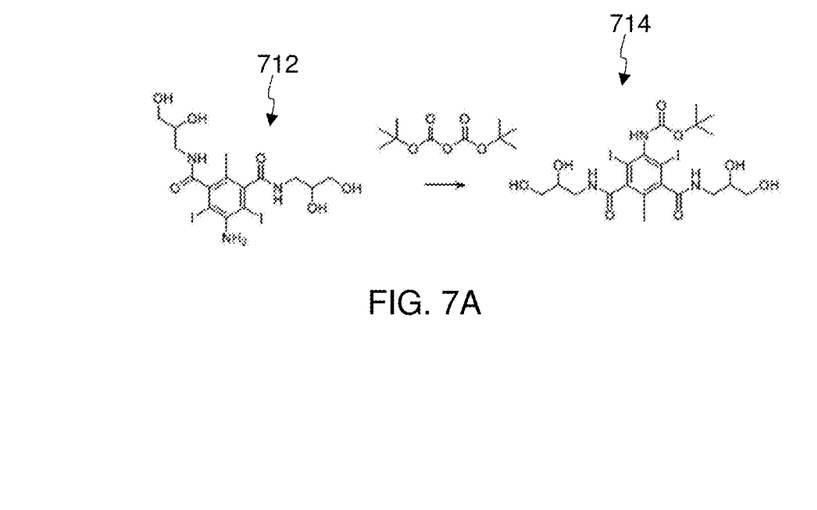
FIGS. 7A-7D schematically illustrate a method of forming a multi-arm polymer having branched reactive radiopaque end groups, in accordance with an embodiment of the present disclosure.
Figure 7B:
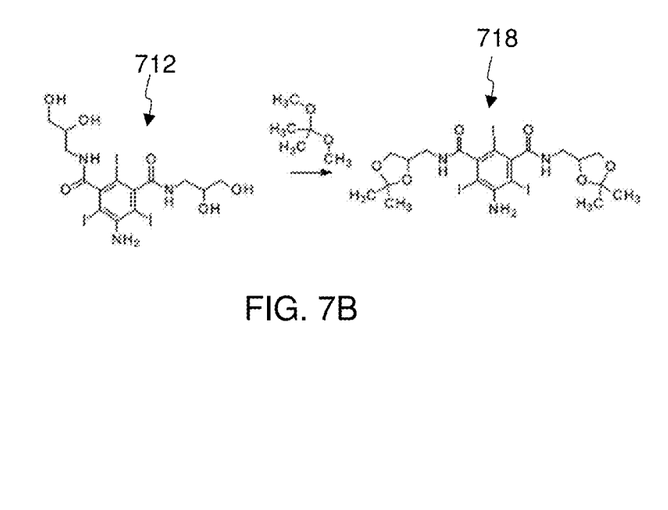
Figure 7C:
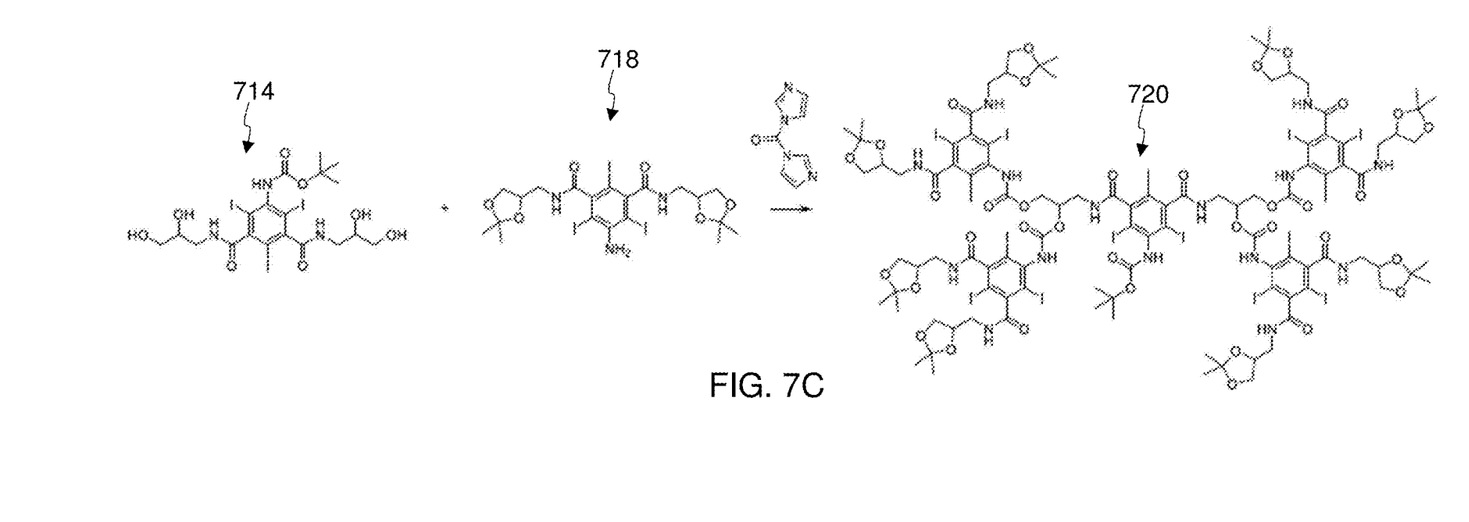
Figure 7D:
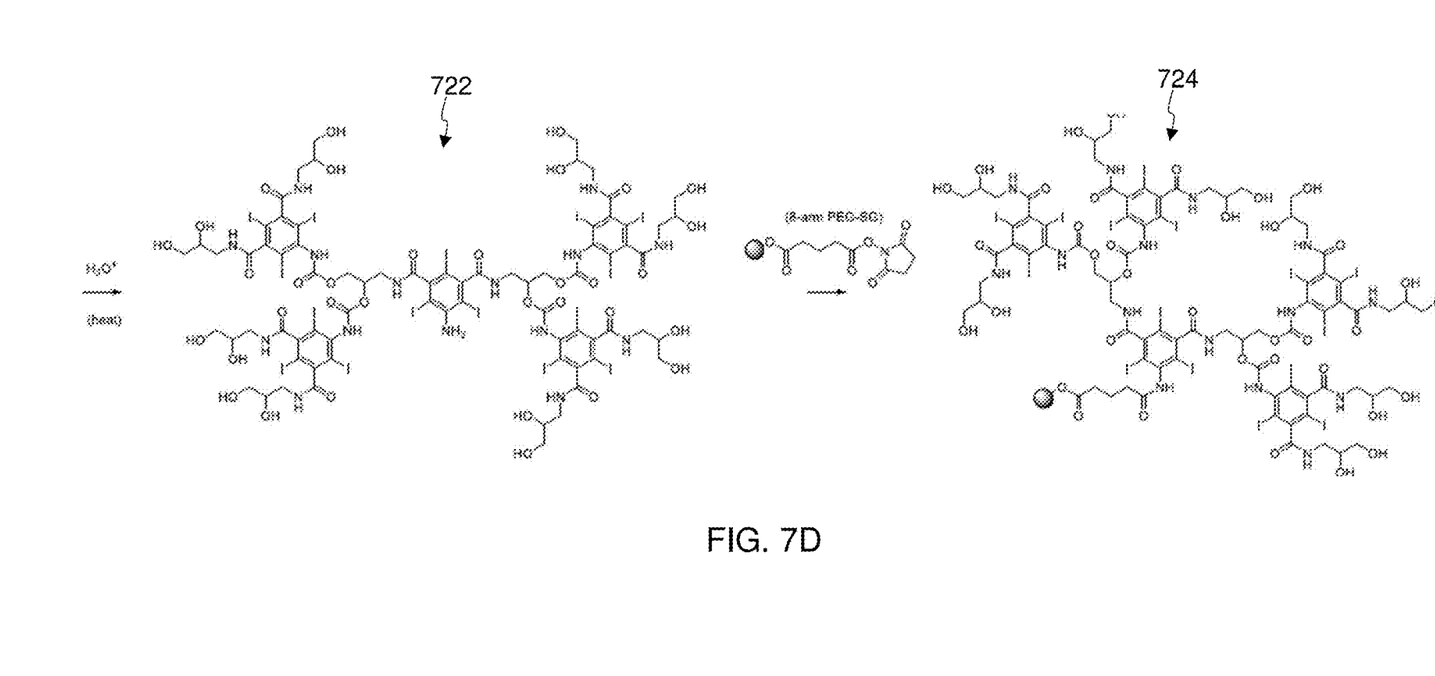

In another approach shown in FIGS. 7A-7D, an amino-substituted iodinated compound (e.g., an amino-substituted hydrophilic triiodoaniline compound 712, such as 5-amino-$N^1,N^3$-bis(2,3-dihydroxypropyl)-2,4,6-triiodoisophthalamide (CAS No. 76801-93-9) or 5-amino-$N^1,N^3$-bis(2,3-dihydroxypropyl)-2,4,6-triiodo-$N^1,N^3$-dimethylisophthalamide (CAS No. 69232-66-2)) is reacted with di-tert-butyl dicarbonate in the presence of a base to form a tBoc-protected triiodoaniline compound 714. Also, as shown in FIG. 7B, an amino-substituted iodinated compound (e.g., an amino-substituted hydrophilic triiodoaniline compound 712) is reacted with 2,2-dimethoxypropane to form an acetonide-protected triiodoaniline compound 718. Then, as shown in FIG. 7C, the tBoc-protected triiodoaniline compound 714 and the acetonide-protected triiodoaniline compound 718 are reacted in the presence of the presence of a suitable agent for amide coupling, such as carbonyldiimidazole or EDC, whereby the amine group of compound 718 is coupled to the hydroxyl groups of compound 714 to form compound 720. Subsequently, as shown in FIG. 7D, compound 720 is exposed to hydronium ions and heat, thereby deprotecting the acetonide-protected hydroxyl groups and deprotecting the tBoc-protected amine group to form compound 722, which has four branches and a triiodoaniline core.

As with iodinated compounds 420 and 518 above, compound 722 is a coupleable branched moiety that comprises a plurality of covalently attached diagnostic and/or therapeutic groups (i.e., iodine atoms) and a functional group (i.e., a primary amine) that is reactive with the reactive end groups (i.e., succinimidyl ester groups) of the multi-arm polymer. For example, as shown in FIG. 7D, compound 720 can be reacted with a sub-stochiometric quantity of the succinimidyl-glutarate groups in a succinimidyl-glutarate-terminated 8-arm PEG molecule (one arm shown) to form a reactive multi-arm polymer in which a first portion of the polymer arms comprise reactive end groups (i.e., a succinimidyl-glutarate group) and wherein a second portion of the polymer arms comprise branched end groups that comprises a plurality of covalently attached diagnostic and/or therapeutic groups (i.e., a plurality of hydrophilic triiodoaniline groups).

Figure 8A:
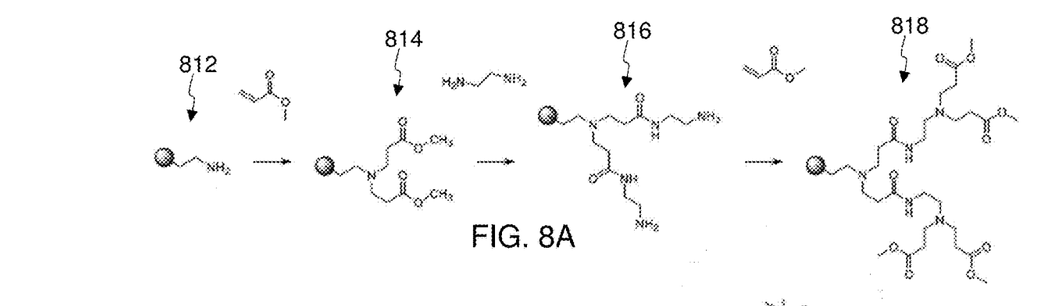
FIGS. 8A-8B schematically illustrate a method of forming a multi-arm polymer having branched radiopaque end groups, in accordance with an embodiment of the present disclosure.
Figure 8B:
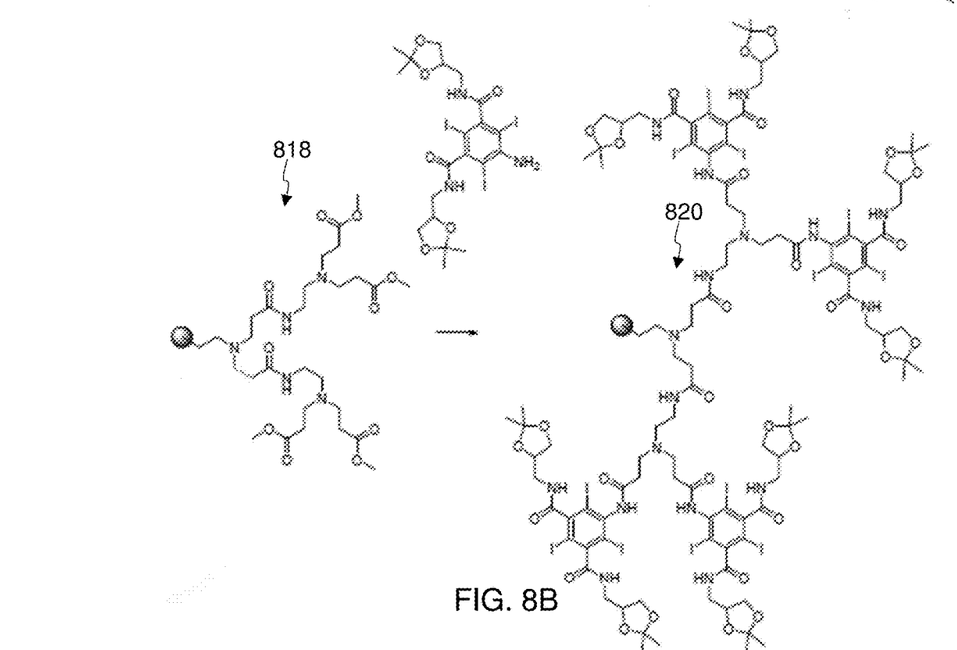

In a further embodiment, and with reference to FIGS. 8A-8B, an amine-terminated multi-arm polymer 812 (one arm shown), for example, a primary-amine-terminated multi-arm PEG, is reacted with methyl acrylate in a Lewis-base-catalyzed Michael addition with the primary amines to yield a di-ester-terminated multi-arm polymer 814 (specifically a di-β-alanine-methyl-ester-terminated multi-arm polymer), which is then reacted with a diamine compound (e.g., ethylenediamine) to form a diamine-terminated multi-arm polymer 816. Then, the diamine-terminated multi-arm polymer 816 is again reacted with methyl acrylate to form a tetra-ester-terminated multi-arm polymer 818. (Note that the prior two steps can be repeated until the desired number of ester groups are obtained.) As shown in FIG. 8B, the tetra-ester-terminated multi-arm polymer 818 can then be reacted with an acetonide-protected triiodoaniline compound (like compound 718 in FIG. 7B) to form a multi-arm polymer 820 having four acetonide-protected triiodoaniline groups and a polyamidoamine core. While the arm of multi-arm polymer 820 shown in FIG. 8B, comprises a branched end group with 4 branches, as indicated above, additional rounds of treatment with methyl acrylate/diamine, will produce a branched end group with 8 branches, 16 branches, 32 branches, and so forth, in dendritic fashion.

In an alternative embodiment, compound 818 may be reacted with a diamine to form a tetramine, followed by reaction of the tetramine with a compound such as 4-((3,5-bis((2,3-dihydroxypropyl)carbamoyl)-2,4,6-triiodophenyl) amino)-4-oxobutanoic acid, which is reactive with amine-terminated polymers.

By selecting a multi-arm polymer 812 for the preceding process that includes hydroxyl-terminated arms in addition to amine terminated-arms (e.g., a heterobifunctional PEG), the resulting multi-arm polymer 820 will likewise have hydroxyl-terminated arms. The hydroxyl-terminated arms of the multi-arm polymer 820 can then be reacted with a cyclic anhydride (e.g., succinic anhydride), followed by reaction with N-hydroxysuccinimde in the presence of a suitable coupling agent, thereby forming providing succinimidyl-glutarate-terminated arms as described above. The acetonide-protected hydroxyl groups may be deprotected by exposure to hydronium ions and heat as previously described.

Using the above and other techniques, reactive multi-arm polymers (e.g., having 2, 3, 4, 5, 6, 7, 8, 9, 10 or more arms) may be formed, which comprise a core and a plurality of polymer arms extending from the core, wherein a first portion of the polymer arms comprise reactive end groups and wherein a second portion of the polymer arms comprise branched end groups having a plurality of covalently attached diagnostic and/or therapeutic groups.

Reactive multi-arm polymers formed as described herein may be water soluble.

Reactive multi-arm polymers formed as described above may be crosslinked with a suitable crosslinking agent, either in vivo or ex vivo, to form a crosslinked hydrogel.

In certain embodiments, the reactive multi-arm polymer may be crosslinked with a multifunctional compound having functional groups that are reactive with the reactive end groups of the multi-arm polymer. For example, in some embodiments, the reactive end groups of the reactive multi-arm polymer are nucleophilic groups and the functional groups of the multifunctional compound group are electrophilic groups. In some embodiments, the reactive end groups of the reactive multi-arm polymer are electrophilic groups and the functional groups of the multifunctional compound are nucleophilic groups. In particular embodiments, the functional groups of the multifunctional compound may be electrophilic groups selected from imidazole esters, imidazole carboxylates, benzotriazole esters, or imide esters, including N-hydroxysuccinimidyl esters. As another example, the functional groups of the multifunctional compound may be nucleophilic groups selected from amine groups and thiol groups.

In some embodiments, the reactive end groups of the reactive multi-arm polymer and the functional groups of the multifunctional compound react with one another via an amide coupling reaction.

In various aspects, the present disclosure pertains to a crosslinkable system comprising (a) a first composition comprising a reactive multi-arm polymer like that described above, which comprises a core (e.g., a polyol residue, among others) and a plurality of polymer arms extending from the core, wherein a first portion of the polymer arms comprise reactive end groups and wherein a second portion of the polymer arms comprise branched end groups having a plurality of covalently attached diagnostic and/or therapeutic groups (e.g., a first fluid composition comprising the reactive multi-arm polymer or a first dry composition that comprises the reactive multi-arm polymer, to which a suitable fluid such as water for injection, saline, etc. can be added to form a fluid composition) and (b) a second composition comprising a multifunctional compound like that described above, which comprises functional groups that are reactive with the reactive end groups (e.g., a second fluid composition comprising the multifunctional compound or a second dry composition that comprises the multifunctional compound, to which a suitable fluid such as water for injection, saline, etc. can be added to form a fluid composition). In some embodiments, the reactive end groups of the reactive multi-arm polymer are electrophilic groups and the functional groups of the multifunctional compound are nucleophilic groups. In some embodiments, the reactive end groups of the reactive multi-arm polymer and the functional groups of the multifunctional compound react with one another via an amide coupling reaction.

As indicated above, in some embodiments, the first portion of the polymer arms corresponds to between 60% and 99% of a total number of the polymer arms in the first composition and the second portion of the polymer arms corresponds to between 1% and 40% of the total number of polymer arms in the first composition.

In addition to the reactive multi-arm polymer, the first composition may further comprise, for example, therapeutic agents and/or contrast agents, among other possibilities.

In addition to the multifunctional compound, the second composition may further comprise, for example, therapeutic agents and/or contrast agents, among other possibilities.

In various embodiments, the system will include one or more delivery devices for delivering the first and second compositions to a subject. For example, the system may include a delivery device that comprises a first reservoir that contains the first composition (e.g., a first fluid composition or a first dry composition to which a suitable fluid can be added to form the first fluid composition) and a second reservoir that contains the second composition (e.g., a second fluid composition or a second dry composition to which a suitable fluid such as water for injection, saline, etc. can be added to form the second fluid composition). During operation, the first and second compositions are dispensed from the first and second reservoirs, whereupon the first and second compositions interact and crosslink with one another to form a hydrogel.

In particular embodiments, the system may include a delivery device that comprises a double-barrel syringe, which includes first barrel having a first barrel outlet, which first barrel contains the first composition, a second barrel having a second barrel outlet, which second barrel contains the second composition, a first plunger that is movable in first barrel, and a second plunger that is movable in second barrel.

In some embodiments, the device may further comprise a mixing section having a first mixing section inlet in fluid communication with the first barrel outlet, a second mixing section inlet in fluid communication with the second barrel outlet, and a mixing section outlet. In some embodiments, the device may further comprise a cannula or catheter tube that is configured to receive first and second fluid compositions from the first and second barrels. For example, a cannula or catheter tube may be configured to form a fluid connection with an outlet of a mixing section by attaching the cannula or catheter tube to an outlet of the mixing section, for example, via a suitable fluid connector such as a luer connector.

As another example, the catheter may be a multi-lumen catheter that comprise a first lumen and a second lumen, a proximal end of the first lumen configured to form a fluid connection with the first barrel outlet and a proximal end of the second lumen configured to form a fluid connection with the second barrel outlet. In some embodiments, the multi-lumen catheter may comprise a mixing section having a first mixing section inlet in fluid communication with a distal end of the first lumen, a second mixing section inlet in fluid communication with a distal end of the second lumen, and a mixing section outlet.

During operation, when the first and second plungers are depressed, the first and second fluid compositions are dispensed from the first and second barrels, whereupon the first and second fluid compositions interact and crosslink to form a hydrogel, which is administered onto or into tissue of a subject. For example, the first and second fluid compositions may pass from the first and second barrels, into the mixing section via first and second mixing section inlets, whereupon the first and second fluid compositions are mixed to form an admixture, which admixture exits the mixing section via the mixing section outlet. In some embodiments, a cannula or catheter tube is attached to the mixing section outlet, allowing the admixture to be administered to a subject after passing through the cannula or catheter tube.

As another example, the first fluid composition may pass from the first barrel outlet into a first lumen of a multi-lumen catheter and the second fluid composition may pass from the second barrel outlet into a second lumen of the multi-lumen catheter. In some embodiments the first and second fluid compositions may pass from the first and second lumen into a mixing section at a distal end of the multi-lumen catheter via first and second mixing section inlets, respectively, whereupon the first and second fluid compositions are mixed in the mixing section to form an admixture, which admixture exits the mixing section via the mixing section outlet.

In additional aspects, the present disclosure pertains to crosslinked products of (a) a reactive multi-arm polymer like that described above, which comprises a core and a plurality of polymer arms extending from the core, wherein a first portion of the polymer arms comprise reactive end groups and wherein a second portion of the polymer arms comprise branched end groups having a plurality of covalently attached diagnostic and/or therapeutic groups and (b) a multifunctional compound that comprises functional groups that are reactive with the reactive end groups. Such crosslinked products may be formed in vivo (e.g., using a delivery device like that described above), or such crosslinked products may be formed ex vivo and subsequently administered to a subject.

In various embodiments, a reaction product of the functional groups of the multifunctional compound with the reactive end groups of the reactive multi-arm polymer are amide linkages.

In certain beneficial embodiments, the reactive end groups of the reactive multi-arm polymers for use in the first composition of the above systems, and for use in forming the above-described crosslinked products (i.e., crosslinked products of the multi-arm polymers described herein with the multifunctional compounds as described herein), may be selected from imidazolyl esters, benzotriazole esters, imide esters, including N-hydroxysuccinimidyl esters and imidazolyl carboxylates, among others.

In certain beneficial embodiments, the multifunctional compound for use in the second composition of the above systems, and for use in forming the above crosslinked products, may be a polyamine. In general, polyamines suitable for use in the present disclosure include, for example, small molecule polyamines (e.g., containing at least two amine groups, for instance, from 3 to 20 amine groups, in some embodiments), comb polymers having amine side groups, and branched polymers having amine end groups, including dendritic polymers having amine end groups.

Particular examples of multifunctional amines which may be used as the multifunctional compound include trilysine, ethylenetriamine, diethylene triamine, hexamethylenetriamine, di(heptamethylene) triamine, di(trimethylene) triamine, bis(hexamethylene) triamine, triethylene tetramine, tripropylene tetramine, tetraethylene pentamine, hexamethylene heptamine, pentaethylene hexamine, dimethyl octylamine, dimethyl decylamine, and JEFFAMINE polyetheramines available from Huntsman Corporation, among others. Further particular examples of multifunctional amines include polypeptides including poly(L-lysine), chitosan, and poly(allyl amine), among others.

Figure 3:
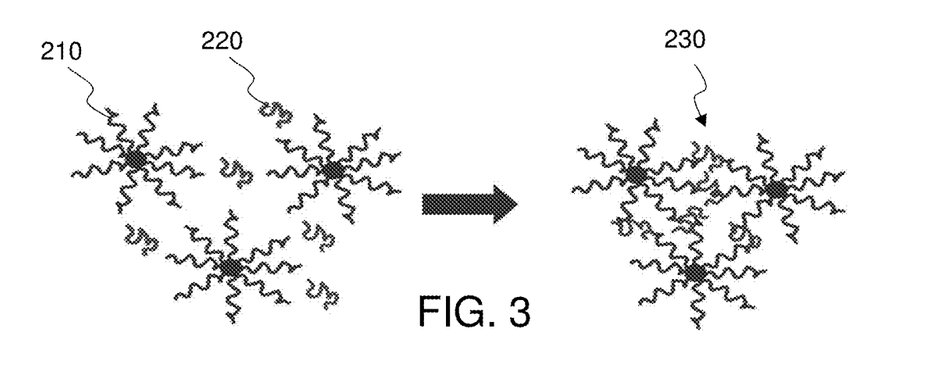
FIG. 3 is a schematic illustration of a method of crosslinking a reactive multi-arm polymer having branched end groups with a multifunctional crosslinking agent, in accordance with an embodiment of the present disclosure.

As shown schematically in FIG. 3, a reactive multi-arm polymer 210 like that described above (e.g., a reactive multi-arm polymer that comprises a core and a plurality of PEG arms extending from the core, wherein a first portion of the polymer arms comprise reactive N-hydroxysuccinimidyl ester end groups and wherein a second portion of the polymer arms comprise branched end groups having a plurality of covalently attached diagnostic and/or therapeutic groups) is crosslinked with a multifunctional compound 220 comprising functional groups that are reactive with the reactive end groups of the multi-arm polymer 210 (e.g., a polyamine such as trilysine) to form a crosslinked product 230.

Compositions comprising the multi-arm polymers as described herein, as well as compositions comprising the cross-linked polymers described herein (i.e., crosslinked products of the multi-arm polymers described herein with the multifunctional compounds as described herein), can be used in a wide variety of biomedical applications, including medical devices, implants, and pharmaceutical compositions.

In various embodiments, compositions can be formed that include the multi-arm polymers described herein as well as one or more additional agents. In various embodiments, compositions can be formed that include the cross-linked polymers described herein as well as one or more additional agents.

Examples of such additional agents include therapeutic agents, and further imaging agents beyond those that may be present in the multi-arm polymer, among others.

Examples of further imaging agents include (a) fluorescent dyes such as fluorescein, indocyanine green, or fluorescent proteins (e.g. green, blue, cyan fluorescent proteins), (b) contrast agents for use in conjunction with magnetic resonance imaging (MRI), including contrast agents that contain elements that form paramagnetic ions, such as $Gd^{(III)}$, $Mn^{(II)}$, $Fe^{(III)}$ and compounds (including chelates) containing the same, such as gadolinium ion chelated with diethylenetriaminepentaacetic acid, (c) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), (d) radiocontrast agents, such as those based on the clinically important isotope $^{99m}Tc$, as well as other gamma emitters such as $^{123}I$, $^{125}I$, $^{131}I$, $^{111}In$, $^{57}Co$, $^{153}Sm$, $^{133}Xe$, $^{51}Cr$, $^{81m}Kr$, $^{201}Tl$, $^{67}Ga$, and $^{75}Se$, among others, (e) positron emitters, such as $^{18}F$, $^{11}C$, $^{13}N$, $^{15}O$, and $^{68}Ga$, among others, may be employed to yield functionalized radiotracer coatings, and (f) contrast agents for use in connection with near-infrared (NIR) imaging, which can be selected to impart near-infrared fluorescence to the coatings of the present disclosure, allowing for deep tissue imaging and device marking, for instance, NIR-sensitive nanoparticles such as gold nanoshells, carbon nanotubes (e.g., nanotubes derivatized with hydroxyl or carboxyl groups, for instance, partially oxidized carbon nanotubes), dye-containing nanoparticles, such as dye-doped nanofibers and dye-encapsulating nanoparticles, and semiconductor quantum dots, among others. NIR-sensitive dyes include cyanine dyes, squaraines, phthalocyanines, porphyrin derivatives and borondipyrromethane (BODIPY) analogs, among others.

Compositions in accordance with the present disclosure include lubricious compositions for medical applications, compositions for therapeutic agent release (e.g., by including one or more therapeutic agents in a matrix of the crosslinked polymers, by using the crosslinked polymers to encapsulate one or more therapeutic agents, etc.), and implants (which may be formed ex vivo or in vivo) (e.g., compositions for use as tissue markers, compositions that act as spacers to reduce side effects of off-target radiation therapy, cosmetic compositions, etc.).

What is claimed is:

1. A system comprising:
    (a) a first composition comprising a multi-arm polymer comprising three or more polymer arms, wherein a first portion of the polymer arms comprises a reactive end group selected from the group consisting of imidazole esters, imidazole carboxylates, benzotriazole esters, or imide esters, and wherein a remaining portion of the polymer arms comprises a branched end group that comprises between 3 and 7 branches, each comprising a covalently attached monocyclic or multicyclic aromatic structures that comprises (i) a plurality of $C_1$-$C_4$-hydroxyalkyl groups and (ii) a plurality of radiopaque functional groups or a plurality of radionuclide groups, wherein the first portion of the polymer arms corresponds to between 60% and 95% of a total number of the polymer arms in the first composition and wherein the second portion of the polymer arms corresponds to between 40% and 5% of the total number of the polymer arms in the first composition; and
    (b) a second composition comprising a multifunctional compound that comprises reactive functional groups selected from the group consisting of amine groups and thiol groups that are reactive with the reactive end group such that a crosslinked reaction is formed.

2. The system of claim 1, wherein the multi-arm polymer comprises five or more polymer arms.

3. The system of claim 1, wherein the reactive functional groups are amine groups.

4. The system of claim 1, wherein the multifunctional compound is a polyamine.

5. A crosslinked reaction product of the first and second compositions of claim 1.

6. The system of claim 1, wherein the radiopaque functional groups or the radionuclide groups are iodine groups.

7. The system of claim 1, wherein the multi-arm polymer comprises between five and ten polymer arms.

8. The system of claim 1, wherein the branched end group comprise an acyclic or cyclic hydroxy-polycarboxylic residue core, an acyclic or cyclic polyamine residue core, an oligolysine residue core, or a polyamidoamine core.

9. The system of claim 1, wherein the polymer arms comprise one or more hydrophilic monomers.

10. The system of claim 1, wherein the polymer arms comprise N-vinyl pyrrolidone, ethylene oxide, or a mixture thereof.

11. The system of claim 1, wherein the plurality of polymer arms extends from a polyol residue core.

12. The system of claim 1, wherein the multifunctional compound is a polyamine compound containing from 3 to 20 amine groups.

13. The system of claim 1, further comprising a delivery device that comprises a double-barrel syringe, which includes first barrel having a first barrel outlet, a first plunger that is movable in first barrel, a second barrel having a second barrel outlet, and a second plunger that is movable in second barrel.

* * * * *